Jan. 8, 1963 E. B. LE GRICE Plant Pat. 2,210
ROSA FLORIBUNDA PLANT
Filed Jan. 15, 1958
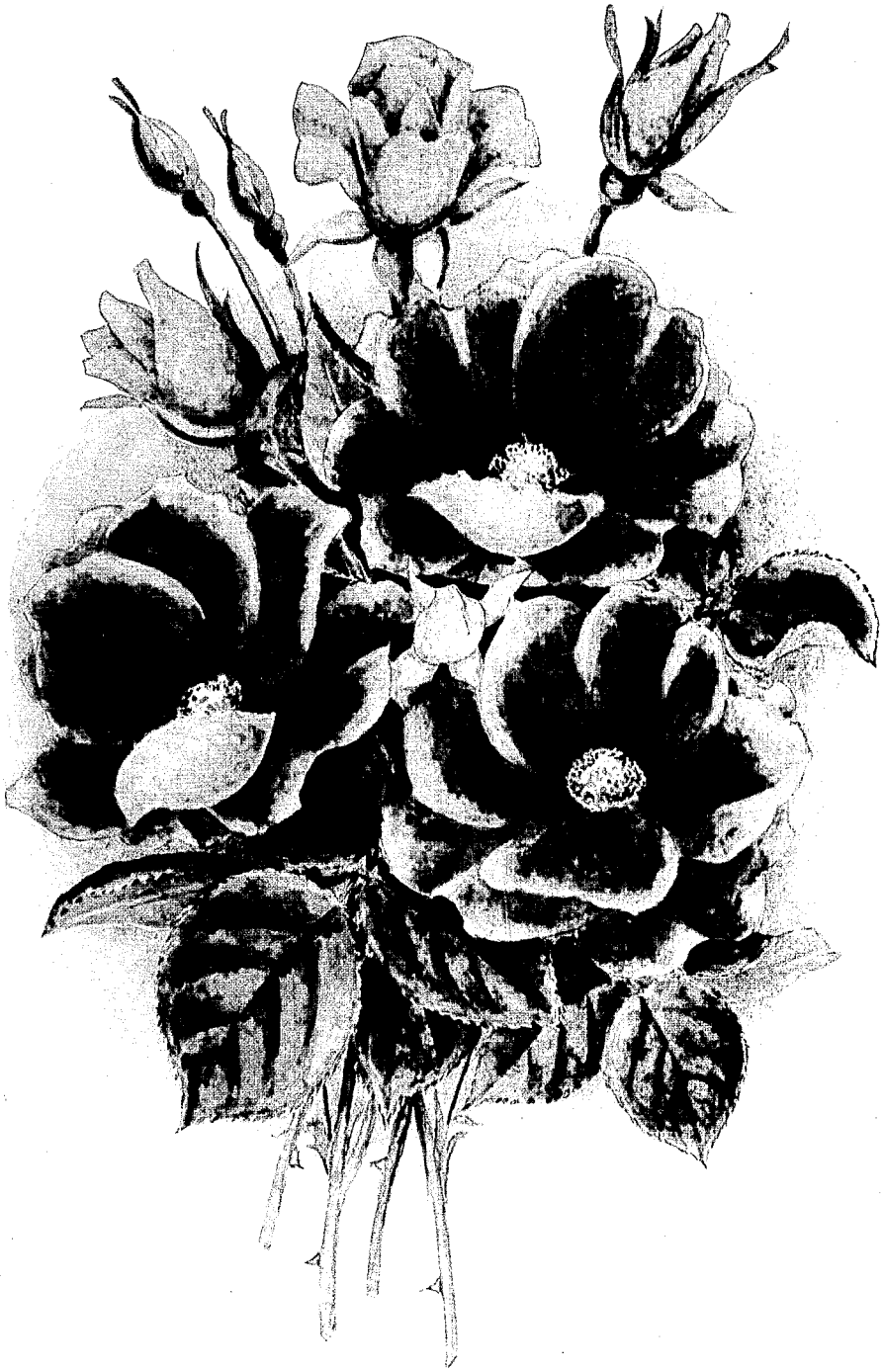
WITNESS
Addison E Avery
INVENTOR
Edward Burton Le Grice,
by:- John A Reynolds,
his ATTY.

United States Patent Office

Plant Pat. 2,210
Patented Jan. 8, 1963

2,210
ROSA FLORIBUNDA PLANT

Edward Burton Le Grice, North Walsham, Norfolk, England

Filed Jan. 15, 1958, Ser. No. 709,128
1 Claim. (Cl. 47—61)

This invention relates to a new variety of rose plant, a Rosa Floribunda hybrid.

The present rose plant was produced originally by me by the deliberate crossing of a Rosa Floribunda, Else Poulsen, as a seed parent, with an unnamed seedling as the pollen parent.

The seed parent, Else Poulsen, was produced by crossing of the rose Orleans Rose, and the rose, Red Star.

The pollen parent was a selected seedling produced by a crossing of the rose, Daily Mail Scented, and the rose, Etoile de Hollande.

The foregoing identified varieties are unpatented.

The new variety was asexually reproduced by me at North Walsham, England, by budding. The new variety has been tested in England, Holland, and Germany.

The drawing shows in color a number of typical stalks with leaves, buds, blooms and thorns.

The exposed plant is in the form of a woody bush of regular contour and rounded at the top. It grows generally to a height of about 2½ feet, and has a spread of about 2 feet. It grows vigorously, but does not grow tall.

The exposed portion of the plant has good resistance to low temperatures when protected, and has fair resistance to low temperature when unprotected. Its resistance both to drought and to wet seasons is good.

For growth it prefers moderate sun and partial shade, with a south and west exposure. It thrives well in any good loam soil of normal drainage.

The main stalks of the plant are slightly branched. For this type of plant, they are relatively stiff and tough, and adequate to support the foliage and blooms well.

The following color terminology is in accordance with the Horticultural Colour Chart of the Royal Horticultural Society.

The new growth of the stalks ranges from Willow Green, Chart 00862, to Pod Green, Chart 061, shaded increasingly to top with Oxblood Red, Chart 00823.

The old growth is a Sage Green, Chart 000761. On both the old and new growth, the color is relatively uniform.

The main stalks range from about 18 inches to 30 inches in length, and are divergent. They have a smooth surface texture with small thorns.

The foliage in general is dense, the leaf arrangement being whorled. The new leaves on the top surface are a Willow Green, Chart 000862, shaded with Oxblood Red, Chart 00823.

The old leaves, on the top surface, are Parsley Green, Chart 00962/2, edged with Oxblood Red, Chart 00823. On the bottom, they are Parsley Green, Chart 00962/3.

In general, the color of the old leaves is variegated, the variegation comprising a more pronounced red shading on the edges of the leaves.

The leaves are relatively large, ranging from 3½ to 6½ inches in length and from 2½ to 4½ inches in width. The leaflets are of the usual shape, being pinnately compound with serrated margins, hastate bases, and acute apices. They are quite thick. On the lower face, they are smooth. Their persistency on the plant is excellent.

The petioles or leaf stems are a Parsley Green, Chart

00962/3. They average in length about 1 inch and are quite strong. They have a smooth surface texture.

The stipules are Lettuce Green, Chart 861, and have serrated edges.

The plant grows and blooms well in temperate regions, preferably at elevations less than 750 feet above sea level. For best blooming it prefers sun, other than a northern exposure, wet cold seasons, and a well drained, rich, slightly acid soil, about pH 6.5.

The plant blooms from early June through October, the blooming being continuous for this period of about five months. Cutting of part of the blooms appears not to change the blooming characteristics or period.

The buds are of medium size, usual in shape, and smooth surfaced. They are borne upright. The petal color, when the sepals first divide, is Spinel Red, Chart 0023, changing to Cardinal Red, Chart 822/1.

When the petals begin to unfurl, the color is Cardinal Red, Chart No. 822/1. When half blown, the color is Currant Red, Chart 821/1, shaded at the base to Chrysanthemum Crimson, Chart 824/1. The reverse, when full blown, is Cardinal Red, Chart 822/2.

The sepals are of the usual shape.

The calyx is usual in shape and size with a smooth texture.

The peduncles average from 1 to 6 inches in length and have a smooth surface texture. The peduncles generally are Pod Green, Chart 061, sometimes shaded with Oxblood Red, Chart 00823/1.

The pedicels average from 1 to 2 inches in length. They have a smooth texture. Their color generally is Pod Green, Chart 061, shaded with Oxblood Red, Chart 00823/1. They are of medium strength.

An increase in the temperature tends to hasten the blooming of the plant.

The blooms are of the single type. They average from 3 to 3½ inches in diameter and an average plant will bear as many as 36 blooms at the same time. The blooms are borne singly and in racemes. On the plant, and when cut, they last from three to four days. They normally have eight petals.

The petalage is Currant Red, Chart 821/1, shaded with Chrysanthemum Crimson, Chart 824/1. The color of the bloom is the same throughout the entire bloom, from the base to the tips of the petals, and on the upper face. On the reverse face, the color is Cardinal Red, Chart 822/2.

The general tonality of the plant from a distance, when it is in bloom, is a Currant Red, Chart 821/1. There is some deepening in color with age.

The petals are smooth, very thick, and have indented centers. They are slightly imbricated and open widely so as to reveal the golden stamens. Petaloids, if present, do not exceed two or three. The persistence of the petals is good, both for cut and uncut blooms.

The fragrance of the blooms is a strong damask. It is of good lasting quality, both in cut and uncut blooms.

The stamens are simple and numerous. In color, they are Aureolin, Chart 3HCC. The filaments are of medium size and, in color, Cadmium Orange, Chart 8. The pollen is Aureolin, Chart 3. The styles and stigmas are Lemon Yellow, Chart 4/2.

The styles are about ¼ of an inch in length. The stigmas are about 1/16 of an inch. Both are plentiful.

On the main stalk, from the base of the plant, the thorns are moderate. On the laterals from the main stalk, they are few. Generally, the thorns are pyramidal. In color they are a chestnut brown. They are unevenly distributed on the main stalk and on the laterals. On the peduncles they are rarely present.

The drawing further illustrates the characteristics of the variety and the following tabulation is a detailed description of the new variety:

*General*

Parentage:

*Seed parent.*—Else Poulsen, resulting from a cross between Orleans Rose and Red Star.

*Pollen parent.*—Unnamed seedling resulting from a cross between Daily Mail Scented and Etoile de Hollande.

Classification: Botanic—Rosa Floribunda hybrid.

*Flower*

Blooming habit:

*Location where observations were made.*—North Walsham, England. National Rose Trial Grounds, Hayward's Heath, England.

*Flowering.*—Continuous for about five months from early June until end of October.

Bud:

*Size.*—Medium.

*Form.*—Elongated.

*Color.*—When sepals first divide, petals are Spinel Red, Chart 0023, changing to Cardinal Red, Chart 822/1; when petals begin to unfurl they are Cardinal Red, Chart 822/1, and when half blown, they are Currant Red, Chart 821/2; when full blown, they are Currant Red, Chart 821/1, shaded to Chrysanthemum Crimson, Chart 824/1. The reverse when full blown is Cardinal Red, Chart 822/2.

*Sepals.*—Long and pointed, and light green in color.

*Calyx.*—Shape and size usual. Aspect—smooth.

*Peduncle.*—Length; from one to six inches. Aspect—smooth. Color—Pod Green, Chart 061; sometimes shaded with Oxblood Red, Chart 00823/1. Strength—medium.

*Opening.*—Rapid, hastened by warmth.

Bloom:

*Size.*—Three to three and a half inches in diameter.

*Borne.*—Singly and in racemes.

*Stems.*—Length, one to two inches; medium strength. Aspect—smooth. Color—Pod Green, Chart 061, sometimes shaded with Oxblood Red, 00823/1.

*Form.*—When first opened, petals widely open, overlapping slightly at edges, and revealing anthers.

*Permanence.*—On the plant, about 3 to 4 days; when cut, about 3 to 4 days.

Petalage:

*Number of petals under normal conditions.*—8.

*Color.*—Inside Currant Red, Chart 821/1, shaded to Chrysanthemum Crimson, Chart 824/1.

*Variegations.*—The inside color is about constant throughout the petals from base to tip, as also is the color of the outside or reverse.

*Discoloration.*—Deepens with age.

Petals:

*Texture.*—Smooth and thick.

*Appearance.*—Great depth of color, as above.

*Form.*—Broad, rounded, with indented center.

*Arrangement.*—Slight imbrication at edges.

*Petaloids in center.*—Few, two to three.

*Persistence.*—Good.

*Fragrance.*—Strong for floribunda, with the quality of damask rose perfume.

*Lasting quality.*—On plant, 3 to 4 days; when cut, 3 to 4 days.

Genital organs:

*Stamens.*—Simple. Color—Aureolin, Chart 3HCC. Arrangement—regular and abundant.

*Filaments.*—Medium. Color—Cadmium Orange, Chart 8.

*Pollen.*—Aureolin, Chart 3.

*Styles.*—¼ of an inch, colored Lemon Yellow, Chart 4/2.

*Stigmas.*—About 1/16 of an inch, colored Lemon Yellow, Chart 4/2.

*Ovaries.*—Plentiful.

*Plant*

Form: A woody bush of regular contour, rounded at top.

Growth: Vigourous, about 2½ feet high and with a 2 foot spread.

Foliage: Dense and whorled.

*Size.*—Medium length from 3½ to 6½ inches and width from 2½ to 4½ inches.

*Quantity.*—Average.

*Color.*—New leaves, on top Willow Green, Chart 000862, shaded with Oxblood Red, Chart 00823. Old leaves, on top, Parsley Green, Chart 00962/2, edged with Oxblood Red, Chart 00823; on their under side, old leaves are Parsley Green, Chart 00962/3.

*Shape.*—Normal.

*Texture.*—Upper face, waxy; lower face, smooth; thick, whorled.

*Edge.*—Serrated; color—Oxblood Red, Chart 00823.

Petiole: Length, about 1 inch, with smooth texture; color—Parsley Green, Chart 00962/3.

*Stipules*: Lettuce Green, Chart 861.

Disease resistance: Appears to have better than average resistance to mildew and blockspot.

Wood:

*New wood.*—Color, Willow Green, Chart 000862, shaded increasingly to top with Oxblood Red, Chart 00823. Bark—smooth.

*Old wood.*—Color, Sage Green, Chart 000761. Bark—smooth.

Thorns:

*Quantity.*—Moderate on main stalks from base, few on laterals.

*Form.*—Short.

*Color.*—Chestnut brown.

*Position.*—Unevenly distributed on main stalks and laterals; rarely present on peduncles.

The most distinctive features and characteristics of the new hybrid rose plant are the depth of color of the blooms and almost maroon shadings, contrasting with the brilliant golden anthers, and the exceedingly sweet perfume.

Having shown and described my new variety of Rosa Floribunda plant, and its manner of asexual reproduction, I claim:

The new and distinct variety of Rosa Floribunda plant herein shown and described.

References Cited in the file of this patent

National Rose Society Annual, of England, for 1949, page 155.